United States Patent [19]

Nairn et al.

[11] Patent Number: 5,672,503

[45] Date of Patent: Sep. 30, 1997

[54] PLANT GROWTH ESTABLISHMENT AND AGENTS FOR USE THEREIN

[75] Inventors: Beverley Janice Nairn, Ohope; Richard Hubert Furneaux, Wellington, both of New Zealand

[73] Assignee: Tasman Forestry Limited, Rotorua, New Zealand

[21] Appl. No.: 470,839

[22] Filed: Jun. 6, 1995

Related U.S. Application Data

[63] Continuation of Ser. No. 46,356, Apr. 9, 1993, abandoned.

[30] Foreign Application Priority Data

Apr. 10, 1992 [NZ] New Zealand ............................ 242308

[51] Int. Cl.$^6$ .............................. C12N 5/04; C12N 1/26; C12N 1/38; A01H 4/00
[52] U.S. Cl. ................................ 435/240.45; 435/240.4; 435/240.46; 435/240.47; 435/240.48; 435/240.5; 435/240.54; 800/DIG. 49; 800/DIG. 51
[58] Field of Search .......................... 435/240.4, 240.45, 435/240.46, 240.47, 240.48, 240.49, 240.5, 240.54; 800/DIG. 51, DIG. 49

[56] References Cited

U.S. PATENT DOCUMENTS 4,960,703  10/1990  Paques et al. .................... 435/240.45

OTHER PUBLICATIONS

Sigma Catalogue 1995, p. 28 Plant Cell Culture Tested Biochemicals.

Oct. 12, 1992 Letter from Research Organics to Xarma Pty Ltd.—Description of Medium Solidifiers for plant tissue culture.

Arnott et al. 1974. J. Mol. Biol. 90:269–284.

Pochet et al. 1990. Med.Fac. Landbouww. Rijksuniv. Gent. 55/4:1411–1413.

Debergh et al. 1981. Physiol. Plant. 53:181–187.

Sigma Cell Culture Reagents®. 1991 Catalogue/Price List pp. 128–129.

Pochet et al. 1991. Plant Cell Reports. 10(8):406–409.

*Primary Examiner*—David T. Fox
*Assistant Examiner*—Thomas Haas
*Attorney, Agent, or Firm*—Ladas & Parry

[57] ABSTRACT

Method for inhibiting vitrification of plants of the Pinus species and Eucalyptus species. In the method, anti-vitrification agents containing one or more sulfated polysaccharides are used. The sulfated polysaccharides are preferably free of toxic components. Tissue culture media is also disclosed.

24 Claims, 3 Drawing Sheets

FIG. 1

FIG. 3

13C-NMR Spectrum of TFP-9

PLANT GROWTH ESTABLISHMENT AND AGENTS FOR USE THEREIN

This is a continuation of application Ser. No. 08/046,356 filed on Apr. 9, 1993, now abandoned.

BACKGROUND OF THE INVENTION

This invention relates to agents for use in plant growth. More particularly, the invention relates to agents which promote the growth of plants in tissue culture. The invention also relates to media containing such an agent, processes of producing said media and to products produced when grown on said media. In particular, the invention relates to an anti-vitrification agent.

A major problem when attempting to micropropagate various plants, in particular *Pinus radiata*, is that the shoots become vitrified. The condition results in a loss of multiplication, the failure of plantlets to successfully establish ex vitro, for example, in the glass house, and can result in significant loss due to death of tissue (>90% in some propagation stages). The phenomenon of vitrification has been described in the literature as translucent, vitriescent, glassy or hyper-hydrated.

Belgian Patent No. 904661 (to Pronatec) describes the production of an alleged anti-vitrification material, for use with apple trees, obtained by hydrolysing agar. Biofuture, March 1990, reported that Pronatec continued their research beyond the description in the patent and identified and isolated an active principle in the hydrolysate. The report also states that the molecule was unstable. The teachings in the patent are not reproducible. The conditions given in the patent are stated broadly. The conditions of hydrolysis could range from mild disruption of an agar chain to total degradation to the monomeric saccharides and degradation products thereof. There is no specific method given taking specifically identified agars, and treating them with a definite amount of acid for a specific time.

Agar is a term used to describe gelling polysaccharides that occur naturally in certain red seaweeds, particularly in Gracilaria, Gelidium and Pterocladia species. The purest form of agar is agarose, a linear polymer composed of alternating 3-linked-β-D-galactopyranosyl and 4-linked-3-6-anhydro-α-L-galactopyranosyl residues. Depending on the seaweed source and the extent to which it is purified during its manufacture, commercial agar can additionally have a range of other substances and/or substituents such as various methylation levels, especially 6-O-methylation on the 3-linked residues in the case of Gracilaria agars. Most agars contain contaminants which are considered undesirable and/or unnecessary for the purpose to which agars are usually used. The purer the agar the higher the value. Contaminants include sulfate half-ester and pyruvate ketal substituents. These contaminants are identified with weak or non-gelling components. Agars are used for their gelling ability and any material which does not have that ability or reduces it, is obviously undesirable.

We have now found that agar itself when in its purest form as agarose does not have significant antivitrification activity. Hydrolysis of it does not change that activity.

SUMMARY OF THE INVENTION

This invention has as its object the provision of an agent which has an antivitrifiation effect. The agent of this invention is distinguishable from and non-obvious over the disclosure in Belgian No. 904661 and the Biofuture article.

The invention provides as an antivitrification agent (AVA) a sulfated polysaccharide or mixtures thereof.

The sulfated polysaccharide can be used in an impure form, for example, as an extract from seaweed or in as purified a form as is required.

In accordance with the invention it has been found that within some commercial agars and some seaweeds, there are sulfated polysaccharides which have an anti-vitrification effect. There are also other materials which have a toxic effect on growing plants. The ratio of toxic agents to AVA varies from seaweed to seaweed and from extract to extract. It is possible in accordance with the invention that an extract from seaweed and even an agar sold commercially may have a satisfactory toxicity/activity balance and could be used as an anti-vitrification agent. Such agars will not fall within the above generally accepted definition of agar, but there is much loose terminology in commercially available materials. Such commercially available agars may therefore have a higher concentration of sulfated polysaccharides than would normally be the case and hence can perform adequately within the scope of this invention.

Normally however, it will be preferred that the sulfated polysaccharide is in a purified state. This ensures more accurate reproducibility of results. However, this is counterbalanced by the cost factor of obtaining materials from natural sources in a highly purified state and these two factors will be balanced in choosing a commercial product.

The sulfated polysaccharides of the invention will generally be sulfate half-esters which are naturally present in a large number of seaweeds as will be discussed further below. Sulfated polysaccharides that can be used in accordance with the invention can be obtained from other sources e.g. derived from cellulose or dextran. Each saccharide unit can be otherwise substituted, e.g. as methyl ethers or have other branching residues e.g. other sugars such as xylose. Commercially available sulfated polysaccharides for use in the invention include lambda, iota and precursor-rich (i.e. mu and nu) carrageenans and dextran sulfate.

The degree of sulfation and the molecular weight and type of the polysaccharide do have some influence on the anti-vitrification activity. Each of these factors interrelate to a certain extent but the major influence on activity appears to be the degree of sulfation. A higher degree of sulfation has been observed to increase the anti-vitrification activity. Thus a polysaccharide with one or more sulfate half esters per saccharide group is preferred.

The type of polysaccharide does not appear to be critical. Activity has been observed with a fucan, a wide variety of galactans, a xylogalactan, a xylorhamnoglycuronan and various glucans.

The majority of these sulfated polysaccharides can be isolated from seaweeds. They are normally in a sufficiently sulfated state to be used as an AVA in accordance with the invention but if necessary, the invention includes modifying the sulfation characteristics of a polysaccharide which has been isolated from a seaweed or otherwise obtained.

In seaweeds there are substances which are toxic to the growing plant and in any commercial product, the toxic substances will need to be removed. It has been generally noted that the toxic substances appear to be of low molecular weight and can therefore be separated from the AVA or other inert substances by a procedure which utilizes the difference in molecular weights for separation purposes. Dialysis, fractional precipitation, gel filtration and chromatography can be used.

The AVA is usually soluble in water or at least in hot water and a first extract can be obtained by heating the seaweed in hot water. The optimum temperature, time, pH, and volume ratios to be used need to be optimized for each seaweed. Typically extraction is conducted in an aqueous buffer at mildly alkaline (for carrageenans) or mildly acidic (for agars) pH, in the 90°–120° C. temperature range. The solid residue is filtered off and the solute is recovered, e.g. by precipitation, e.g. with a water miscible lipophilic solvent, such as an alcohol or ketone, e.g. isopropanol or acetone. The precipitated material can then be subjected to the separation techniques, e.g. dialysis against fresh water and finally lyophilized.

Dextran sulfate is currently a preferred agent for use in the invention. While its activity is less than a number of other sulfated polysaccharides it has a low toxicity. It is also commercially available in a substantially pure form. Dextran sulfate has shown activity as an anti-vitrification agent, particularly that material with a high molecular weight, for example those made from dextrans in the molecular weight range of 500,000 daltons or greater. The compound can be obtained by esterifying dextran of the desired molecular weight profile with chlorosulfonic acid in a suitable solvent such as pyridine. The degree of sulfation of materials produced in this way can vary but tests on materials having 17–18% sulphur have indicated good activity. Dextran itself is commercially produced from sucrose by certain bacteria such as *Leuconosotoc mesenteroides*, a member of the Lactobacillaceae.

One source of the agent of the invention can be any seaweed containing such an agent. Trial and error will be required to ascertain which seaweeds are suitable to produce the AVA, but currently tested seaweeds which have produced acceptable results are Gelidium, Eucheuma (or Kappaphycus), Chondrus, Aodes, Pterocladia, Sarcodia, Gracilaria, Porphyra, Grateloupia, Gigartina, Chondria, Pachymenia, Iridea, Splachnidium, Catenella, Ulva, and a member of the Solieriaceae.

In accordance with the invention, impure materials containing one or more AVA's can be used. One of the potential useful materials is a "press-fluid" extract. This is produced in the manufacture of agar from various seaweeds as a by-product. This by-product is obtained when the gel obtained on cooling the extract from an agar-bearing seaweed resource is pressed to reduce the water content of the gel. It has been found in accordance with the invention that a number of anti-vitrification agents of use in the invention can be obtained from the press-fluid extract. The extract needs to be treated to remove toxic substances in the manner described previously. A very similar "thaw-water" by-product is obtained if the gel is dewatered by a freeze-thaw process.

Toxicity of a substance is intended to mean within the scope of the invention, effects on the plant which are other than vitrification and which manifest as a gradual decline in the health and growth of the tissues culminating in death, the speed of the decline being proportional to the toxicity. It has been found with some materials which have a high AVA effect, that there is an inherent toxic effect which reduces their potential for commercial use. It is believed that the ratio of anti-vitrification activity to toxicity, can be improved by varying the concentration of the active agent. It has been observed that the relative toxicity of a particular concentration of an AVA can vary among different clones of the same species of tree. Between different species of tree, there is usually a greater variation of AVA effect and the degree of toxicity for the same sulfated polysaccharide preparation.

The invention further provides a process for tissue culture of plants comprising incorporating in the tissue culture process, the anti-vitrification agent of the invention in such a manner as to inhibit the vitrification of the plants. The term "tissue culture" as used herein takes its general meaning and includes the growth of cells, including tissues and small pieces of tissue, outside the plant in artificial media. The term is intended to include growth on both solid media and in liquid media. The invention further provides a media for use in tissue culture which contains the said agent plus other materials required for growth of the plant. In accordance with the invention, any plants which are tissue cultured and which suffer from vitrification can be treated with the agents of the invention. The response to the AVAs will vary from plant to plant, but it is envisaged that substantially all vitrification problems will be inhibited or improved by use of one or other of the AVAs of this invention.

The tissue culture method may comprise combining together suitable nutrients for the growth of plants, for example, mineral salts, and a carbon source such as sugar. The ingredients may be combined with the AVA and a gelling media (if required) prior to sterilizing, such as by autoclaving. Alternatively, the AVA may be sterilized separately. When a gelling media has been added the media will solidify. Prior to autoclaving the pH is adjusted generally to around 5.7.

The amount of AVA is chosen to achieve an acceptable antivitrification effect while minimizing the toxic effect. Usually a final concentration of between 0.1 g and 1.0 g/200 mls of final medium is acceptable. With impure forms of AVA greater amounts may be needed.

The process of the invention has particular application to tissue culture using a liquid medium. This enables the AVA and other nutrients in the medium to be monitored and where necessary additional nutrients and/or AVA added to maintain an optimum level.

In liquid culture, media are prepared with modified Quoirin le Poivre minerals. AVA samples are usually added (to control vitrification) prior to autoclaving. Media are than poured into flat bottles to assist aeration. Meristematic tissue of *Pinus radiata* is added and incubated under lights at 25° C. In liquid media, cultures without AVA rapidly became vitrified and die. Using the AVA of this invention the cultures can readily proliferate.

The invention particularly relates to tissue culture of forestry plants, particularly Pinus spp, such as *Pinus radiata,* and Eucalyptus spp. *Pinus radiata* suffers quite significantly from vitrification during tissue culture and use of AVAs in accordance with the invention has been found to give significant improvement.

The invention will be described with reference to the following non-limiting examples. Examples 1 to 14 illustrate processes for obtaining an AVA of the invention. The materials obtained by the methods possess anti-vitrification activity. Further processing in general is necessary to remove the toxic substances in the samples.

BRIEF DESCRIPTION OF THE DRAWINGS

FIG. 1: chemical structure of agarobiose-type repeating units (I and II) and precursor-type repeating units (III, IV and V).

FIG. 2: NMR spectrum of TFP-7.

FIG. 3: NMR spectrum of TFP-9.

DESCRIPTION OF THE PREFERRED EMBODIMENTS

EXAMPLE 1

Isolation of TFP-7

This material was obtained from Difco Bacteriological Grade Agar (Lot No. 760112 supplied by Difco Laboratories, Detroit, Mich., U.S.A.) by leaching of aqueous gels made from the agar and purified by dialysis.

Thus gels containing 5-10% agar were prepared by dissolution of agar in an autoclave at 120° C. for 30 min, allowed to set at room temperature and conditioned at 4° C. overnight. The gels were cut into strips and equilibrated with gently stirred distilled water (3 volumes) for 24 hours at room temperature. The now light yellow leachate was filtered through sintered glass (porosity 3) and concentrated to ca one tenth of its original volume on a rotary evaporator at ca 20 torr, 50° C. bath temperature. The gel strips were re-equilibrated with a further 3 volumes of water, which was processed as above. The combined, concentrated leachate was freeze-dried to a fawn-coloured solid. Yield=18.73 g (8.5%) from 220 g of Agar.

The leachate (18.7 g) was placed in Visking dialysis tubing with deionized water, and dialysed against several changes of gently stirred deionized water. Some of the leachate sample was initially insoluble, but most dissolved as dialysis progressed.

The retentate was pressure filtered through a bed of celite on a glass fibre sheet (GF/A) to remove the small amount of remaining insoluble material, and freeze-dried to a fawn-coloured solid, TFP-7; Yield=11.86 g (63% recovery from leachate; 5.4% yield from agar).

EXAMPLE 2

Preparation of TFP-8A and TFP-8B From TFP-7 by Acid Treatment

Crude Fraction TFP-7 (1.76 g) was heated in aqueous hydrochloric acid (0.1M, 59 ml) at 80° C. for 1 h with stirring. The resulting cloudy solution was separated into two equal fractions.

The first half was evaporated to dryness on a rotary evaporator (bath temp. 40° C.). The resulting syrup was dried overnight in vacuo over solid KOH, redissolved in water (whereupon the pH was still 1), neutralized with aqueous NaOH, filtered through a glass fibre filter (GF/A) under pressure to remove insoluble material, and freeze-dried to yield TFP-8A, 0.94 g. This material includes a calculated 0.18 g NaCl from the neutralization step, implying an 86% recovery of material.

The second half was neutralized with NaOH, dialysed against deionized water, pressure filtered through glass fibre filter (GF/A) at 5 psi to remove insoluble material, and freeze-dried to yield TFP-8B, 0.61 g (69% recovery).

As results in Table 3 show the hydrolysis reduced the activity of the starting material TFP-7.

EXAMPLE 3

Preparation of TFP-9 from TFP-7 by Alkali Treatment

Crude Fraction TFP-7 (0.88 g) was dissolved in hot water (15 ml) with stirring. Aqueous NaOH-NaSH$_4$ (4 and 0.2M resp., 15 ml) was added, and heating continued for 3 hr at 80° C. The mixture was cooled, neutralized with acetic acid (3.6 ml), dialysed against aqueous acetic acid (pH 4) then water and freeze-dried to yield TFP-9, 0.67 g (76% recovery).

EXAMPLE 4

Preparation of Materials (TFP-14A and TFP-14B) from Press-Fluid

The manufacture of agar from Pterocladia species can be conducted by sequentially: (a) washing of the dried weed and bleaching of the residue, (b) extraction of the weed with hot water at mildly acidic pH, (c) gelation of the extract, (d) dewatering by pressing of gelled slabs, and (e) drying the resulting dewatered agar slabs.

Pterocladia extract usually contains about 1.2% agar (with a 12% moisture content). After subjecting the gelled extract to a pressing process, the residual pressed-gel usually contains 18-20% solids.

A sample of press-fluid (0.88 liters) from a commercial agar process (Coast Biologicals Limited) was freeze-dried to yield TFP-14A as a white solid (5.61 g). The concentration of TFP-14A in the press fluid is thus 0.638%.

A further sample of press fluid (1.00 liters) from a commercial agar process (Coast Biologicals Limited) was dialysed against distilled water (4×4 liters) over several days, then the retentate was freeze-dried to yield TFP-14B as a white solid (5.18 g). The concentration of TFP-14B in the press fluid is thus 0.518%.

Dialysis removed only ca 20% of the solids content of the press-fluid. This is consistent with the fact that the weed is subjected to pretreatment, involving washing to remove sea salts, and bleaching, prior to extraction.

From these figures, in combination with the 0.638% solids content determined for the press-fluid, the following mass flow can be calculated:

EXAMPLE 5

Separation of TFP-25A and TFP-25B from TFP-9 on the Basis of Solubility in Aqueous Ethanol TFP-9 (1.0 g) was dissolved in water (50 ml), then the following aliquots of ethanol were added, with the mixtures being left to stand at 4° C. overnight between each addition: 10, 20, 30, 50, 140 mls. At each stage the solution was quite turbid. A precipitate formed only when a total of 250 mls of ethanol had been added, ie the solution was 83% ethanol. The precipitate was collected by centrifugation, washed with fresh 83% ethanol, and redissolved in hot water (a trace of brown sludge remained undissolved) and freeze-dried to yield TFP-25A (0.41 g, 41%).

The supernatant was diluted to 500 ml then 1 liter with ethanol (i.e. 90 then 95% ethanol) but no further precipitation occurred. The solution was then concentrated, redissolved in water and freeze-dried to yield TFP-25B (0.46 g, 46%).

EXAMPLE 6

Preparation of Samples TFP-32A from Agar Prepared Commercially from an Indonesian Supply of Gelidium The sample of Indonesian Gelidium agar (Lot 2242, 250 g) supplied by Coast Biologicals Ltd, was dissolved in a pressure cooker to form a 5% gel (total volume ca 5 liters) and allowed to set at room temperature overnight. The gel was cut into strips and equilibrated with 3 volumes of gently stirred deionized or distilled water, for at least 6 h. The "dialysis" process was repeated with two fresh lots of water. The resulting "leachate" was concentrated in vacuo, and freeze-dried to give a crude "leachate" TFP-29 (9.33 g).

This crude "leachate" was further purified by redissolution in water (250 ml) in a pressure cooker. The hot solution was filtered through a wire mesh from undissolved silica gel particles. The silica gel originated from the deionized water used above. These silica gel particles were washed with fresh water, extracted in a pressure cooker with fresh water and again separated by filtration through a wire mesh. The gel particles were collected and dried to give TFP-31A (1.38 g).

The combined filtrates and washings were concentrated in vacuo and stored at 4° overnight, whereupon they set to a gel of moderate strength. The gelling component was isolated by a freeze-thaw process, with the gel matrix being pressed to separate as much thaw-water as possible. The gel matrix was redissolved in fresh water and resubjected to the freeze-thaw process. The resulting gel matrix was dried at 60° and powdered to give TFP-32A as a brown solid (1.85 g).

The combined thaw-waters were concentrated, dialysed against distilled water (3×10 vol.) and lyophilized to give TFP-32B (3.57 g, 1.4% from agar).

In the isolation of the desired TFP-32B from TFP-29 the mass balance shows that of the initial 9.33 g of TFP-29, 6.30 g is accounted for by recovered solids (TFP-31A+32A+32B). Thus 2.53 g of the original material is lost either as salts and small organic molecules during the dialysis process, or through handling losses.

From measurements of the volumes of thaw-water and gel matrix it could be shown that the gelling component TFP-32A contains <5% of the total weight of the non-gelling component TFP-32B, ie <0.179 g. Thus TFP-32A contains no more than 10% by weight of the components in TFP-32B.

The major differences observed in processing the original Difco Agar (Example 1) as compared to the Gelidium Agar were:

a The Difco Agar gave a cold-water soluble, dialysed extract (TFP-7) in 5.4% yield, whereas the equivalent material (TFP-32B) from Gelidium Agar was obtained in only 1.4% yield.

b Upon concentration, the cold-water leachate from the Gelidium Agar formed a reasonably firm gel. This did not occur in the case of the Difco Agar. The gelling component was largely separated from the non-gelling component by a double freeze-thawing process.

EXAMPLE 7

Preparation of TFP-35 from Press-Fluid from Gelidium Agar Extraction Process

TFP-35 (2.09 g) was obtained from press-water supplied by Coast Biologicals Limited from the commercial production of agar from Indonesian supplies of Gelidium by filtration/clarification through a Whatman GF/D filter, concentration of the filtrate (1566 ml) to 200 ml, dialysis against distilled water (3×10 vol.) and freeze-drying.

EXAMPLE 8

The following commercially available materials were trialed for their antivitrifying effect:

| Code Name | Name | |
|---|---|---|
| TFP-26C | Lambda Carrageenan (Sigma C3889) | |
| | Origin: | The aqueous KCl-soluble fraction of the extract from *Gigartina aciculaire* and *G. pistillata* which grow together in the sea. |
| | Supplier: | Prepared for Sigma by FMC Bioproducts (Rockland, Marine, USA). |
| | Structure: | As reported by T T Stevenson and R H Furneaux, Carbohydr. Res., 210 (1991) 277–298. |
| TFP-33C | Iota Carrageenan (Sigma C4014) | |
| | Origin: | Extracted under alkaline conditions (usually calcium hydroxide) from *Eucheuma 'spinosa'*. For a detailed description of thin and related seaweeds, see G A Santos, Aquatic Botany 36 (1989) 55–67. |
| | Supplier: | Sigma |
| TFP-33D | Kappa Carrageenan (Sigma C1263) | |
| | Origin: | Extracted under alkaline conditions from *Eucheuma 'cottonii'* also known as a Kappaphycus species. For a detailed description of thin and related seaweeds, see G A Santos, Aquatic Botany 36 (1989) 55–67. |
| | Supplier: | Sigma |
| TFP-39A | Pentosan Polysulphate (Sigma P8275) | |
| | Origin: | Lot 114F0194. From chemical sulfation |
| | Supplier: | Sigma |
| TFP-39F | Lambda Carrageenan | |
| | Supplier: | FMC Bioproducts Limited, as SeaKem XP8012. |
| | Origin: | Extracted from tetrasporic life phase plants of *Chondrus crispus* grown in mariculture in Nova Scotia, Canada. |
| | Composition: | As reported by T C S Dolan and D A Rees, J. Chem. Soc., (1965) 3534–3539. |
| TFP-46A | Sodium cellulose sulphate | |
| | Supplier: | Dextran Products Limited, USA |
| | Origin: | Lot No. 890410B, April 1989 Prepared by chemical sulfation of cellulose. |
| GP-309 | Viscarin GP 309 | |
| | Supplier: | FMC Corporation, USA |
| | Origin: | Lot No. 952701 |
| TFP-51-A | Xappa-Carrageenan from *Chondrus armatus* | |
| | Supplier: | The Institute of Bioorganic Chemistry, Far East Branch, Russian Academy of Sciences |
| | Origin: | Grade A |
| TFP-51B | Kappa-Carrageenan from *Chondrus armatus* | |
| | Supplier: | As for TFP-51A |
| | Origin: | Grade B |

Dextran Sulfate Samples

All samples prepared by chemical sulfation of dextrans.

| | | |
|---|---|---|
| TFP-39B | Supplier: | Sigma |
| | Origin: | Cat. No. D-7140, Lot 18F0532. |
| | Composition: | Av. MW of dextran 500,000 daltons. |
| TFP-39C | Supplier: | Sigma |
| | Origin: | Cat. No. D7037, Lot 109F04641 |
| | Composition: | Average MW of dextran ca 5,000 daltons. |
| TFP-39D | Supplier: | Sigma |
| | Origin: | Cat. No. D4911, Lot 99F-0458. |
| | Composition: | Average MW of dextran ca 8,000 |
| TFP-39E | Supplier: | Sigma |
| | Origin: | Cat. No. D6001, Lot 11H0523 |
| | Composition: | Average MW of dextran ca 500,000 daltons, prepared by a different manufacturer from Cat. No. D-7140. |
| TFP-42C | Supplier: | Nacalai Tesgue, Japan |

| | | |
|---|---|---|
| | Origin: | Cat. No. 750-00 DS-500 |
| | Composition: | Average MW of dextran ca 500,000 daltons. |
| TFP-43A | Supplier: | Ueno Fine Chemicals Industries Limited, Japan |
| | Composition: | Average MW of dextran ca 8,000 daltons. |
| TFP-43B | Supplier: | Dextran Products Limited, USA. |
| | Origin: | Lot No. DS8-O1W-53 |
| | Composition: | Average MW of dextran ca 8,000 daltons. |
| TFP-43C | Supplier: | Dextran Products Limited, USA |
| | Origin: | Lot No. D540-11N75 |
| | Composition: | Average MW of dextran ca 40,000 daltons. |
| TFP-43D | Supplier: | Dextran Products Limited, USA |
| | Origin: | Lot No. DSM-55 |
| | Composition: | Average MW of dextran ca 500,000 daltons. |

EXAMPLE 9

The following seaweed extracts were tested for antivitrification activity:

| Code Name | Identity | |
|---|---|---|
| TFP-26B | Xylogalactan sulfate from *Sarcodia flabellata* | |
| | Origin: | Seaweed collected at Princess Bay, Wellington in April 1981. This polymer was extracted from the seaweed with hot water and precipitated with 4 volumes of acetone. It was purified by precipitation with cetyl trimethyl-ammonium bromide at pH 1.5, redissolution in aqueous 4M NaCl which was washed with n-pentanol, dialysis against distilled water and lyophilization. |
| | Composition: | A sulfated xylogalactan (xylose and galactose component sugars in a ca. 8:92 ratio) with substantial levels of pyruvate as a ketal substituent on positions-4,6 of 3-linked galactosyl-2-sulphate residues. |
| TFP-26F | Xylogalactan sulfate from *Chondria macrocarpa* | |
| | Origin: and Composition: | As described in R H Furneaux and T T Stevenson, Hydrobiologia 204/205 (1990) 615–620. |
| TFP-26I | Agar from *Gracilaria chilensis* (previously *G. secundata* f. *pseudoflagellitera*) | |
| | Origin: | Unmodified gelling component extracted from weed collected in Eastbourne, Wellington. |
| | Composition: | As described in I J Miller and R H Furneaux, Botanica Marina 30 (1987) 427–435. |
| TFP-26J | Non-gelling galactan sulfate from *Gracilaria chilensis* (previously *G. secundata* f. *pseudoflagellitera*) | |
| | Origin: | Non-gelling thaw-water polysaccharide extracted from weed collected in Ngakuta Bay and purified by treatment with amyloglucosidase and dialysis. |
| | Composition: | As described in I J Miller and R H Furneaux, Botanica Marina 30 (1987) 427–435. |
| TFP-33E | Porphyran from *Porphyra columbina* | |
| | Origin: | Unmodified extract from weed collected from Lyall Bay, Wellington 22 September 1989. |
| | Composition: | As described in D J Brasch et al, Carbohydr. Res. 97 (1981) 113–125. |
| TFP-33F | Galactan sulfate from *Grateloupia pinnata* | |
| | Origin: | Unmodified extract from weed collected from Ngakuta Bay, Queen Charlotte Sounds, 11 October 1981. |
| TFP-33G | Galactan sulphate from *Grateloupia intestinalis* | |
| | Origin: | Unmodified extract from weed collected from Titahi Bay, October 1980. |
| TFP-33J | Lambda-type carrageenan from tetrapsoric *Gigartina decipiens* | |
| | Origin: | Weed collected from Eastbourne, Wellington, December 1983. |
| | Composition: | As described in R Falshaw and R H Furneaux, "Carrageenan from the tetrasporic phase of *Gigartina decipiens* (Gigartinaceae, Rhodophyta)" Carbohydr. Res., in press. |
| TFP-37A | Lambda-type carrageenan from tetrasporic *Gigartina chapmanii* | |
| | Origin: | Weed collected from Ngakuta Bay, Queen Charlotte Sounds, September and October 1980. |
| TFP-37B | Lambda-type carrageenan from tetrasporic *Gigartina clavifera* | |
| | Origin: | Weed collected from Kaikoura, 31 March 1984. |
| TFP-38A | Galactan sulfate from *Aodes nitidissima* | |
| | Origin: | Weed collected from Tauranga in early 1982. |
| TFP-38B | Galactan sulfate from *Pachymenia lusoria* | |
| | Origin: | Weed collected from Constant Bay, January 1982. |
| TFP-47 | Carrageenan from cystocarpic *Gigartina decipiens* | |
| | Origin: | Weed was collected in March 1991 from Eastbourne, Wellington and air dried. Polysaccharide extracted into water (500 ml per 10–15 g air-dried weed) at 90° for 1.5 h. Extracts filtered, cooled, treated with amyloglucosidase to digest starch, reheated to eliminate enzyme activities, and filtered. Polysaccharide precipitated with 3 vol propan-2-ol, redissolved in water, purified by dialysis, and recovered by lyophilization. |
| | Composition: | A kappa-type carrageenan with about 85:15 ratio of kappa-and iota-residues, and less than 5% precursor (mu + nu) residues. |
| TFP-48 | Carrageenan from cystocarpic *Gigartina circumcincta* | |
| | Origin: | Weed was collected in March 1991 from Eastbourne, Wellington and air dried. Polysaccharide extracted and purified as for TFP-47 but without amyloglucosidase treatment. Yield 35 wt. %. |
| | Composition: | Kappa-type carrageenan with kappa-, iota-, and precursor (mu + nu) residues in approximately the ratio 34:46:20 by $^{13}$C—NMR spectroscopy and chemical analysis. |
| TFP-49A | Cold-water soluble *Eucheuma cottonii* carrageenan | |
| | Origin: | This alga is now known as *Kappaphycus alvarezii*, and is the source of commercial kappa-carrageenan. Weed obtained from Kiribati. It had been washed with fresh water and dried. A sample of this weed was soaked overnight in water (10 vol) at ambient temperature. The extract was drained from the weed, filtered, concentrated, dialysed and lyophilized. Yield 1.65 wt. %. |
| | Composition: | An iota-carrageenan with an additional ca 50–70% methylation on 0–6 of the 3-linked galactosyl residues, and some precursor type residues, by $^{13}$C—NMR spectroscopy and chemical analysis. These analyses confirm the results of C Bellion et al [Carbohydr. Res. 119 (1983) 31] on material obtained in a different manner from the same seaweed. |
| TFP-49B | Kappa-carrageenan from *Eucheuma cottonii* | |
| | Origin: | Same weed as for TFP-49A (30 g) was |

| Code Name | Identity | |
|---|---|---|
| | | extracted with 0.5M aqueous potassium chloride (600 ml) at 50° C. for 48 h, then dried. A sample of the residue (10 g) was then extracted with water (500 ml) at 100° for 2.5 h. The extract was filtered, dialysed against 0.1M aqueous sodium chloride, filtered and lyophilized. |
| | Composition: | Identical to commercial kappa-carrageenan by $^{13}$C—NMR spectroscopy. |
| TFP-50 | Lambda-type carrageenan from tetrasporic *Gigartina circumcincta* | |
| | Origin: | Weed was collected from Eastbourne, Wellington in March 1981 and air-dried. Polysaccharide was extracted from air-dried weed (10 g) with water (500 ml) for 2 h at 100°, and filtered. Polysaccharide was preipitated with propan-2-ol, redissolved in water, purified by dialysis, and recovered by lyophilization. |
| | Composition: | A complex sulphated galactan having glycosyl residues characteristic of lambda-, pi-, and a previously unreported repeating disaccharide constituent residues. |
| TFP-57A | Carrageenan from Orakei weed | |
| | Origin: | A red seaweed in the family Solieriaceae of otherwise uncertain taxonomic identity was collected from Orakei Basin, Auckland in June 1992, and air dried. Air-dried weed (5 g) was soaked for 1 h in water (300 ml) containing sodium bicarbonate (1.26 g), then heated in a boiling water bath for 4 h. After filtration and cooling, amylase was added and the solution was allowed to stand overnight. The solution was then reheated, refiltered, and allowed to cool. Dialysis against 3 changes of distilled water, followed by lyophilization gave the polysaccharide. |
| | Composition: | An iota-cargageenan with an additional ca 12% methylation on 0-6 of the 3-linked galactosyl residues, as determined by $^{13}$C—NMR spectroscopy and chemical analysis. |
| TFP-57B | Alkali-modified carrageenan from Orakei-weed | |
| | Origin: | TFP-57A (1.5 g) was treated with an aqueous solution (450 ml) containing NaBH$_4$ (0.15 g) and NaOH (18 g) at 80° C. for 3.5 h. The resulting solution was cooled, neutralized with glacial acetic acid, and the carrageenan isolated by dialysis and lyophilization. |
| TFP-56 | Fucoidan from *Splachnidium rugosum* | |
| | Origin: | This material was obtained from Carina Chemical Laboratories, Lower Hutt. It was prepared from brown seaweed collected at Tauranga Bay, Westport and air dried. The weed was soaked in a dilute solution of mineral acid initially at pH 1 for 2 h, drained off, and washed. The fucoidan was then extracted into water at 90° C. for 4 h. The extract was filtered, adjusted to pH 8 with aqueous Na$_2$CO$_3$, treated with charcoal, refiltered, concentrated, dialysed and dried to yield the fucoidan sample. |
| TFP-55 | Lambda-type carrageenan from "*Gigartina radula*" | |
| | Origin: | Isolated from a Chilean seaweed, and supplied by FMC Corporation, USA. Botanical identity of seaweed probably an Iridea species. |
| TFP-59 | Carrageenan from Catenella species | |
| | Origin: | Extracted from Catenella species, probably *C. nipae*, from Thailand. Supplied by Professor S. Chandrkrachang, Srinakarinwiret University, Bangkok, Thailand. |
| | Composition: | Contains near equal proportions of iota- and alpha-carrageenan repeating units by $^{13}$C—NMR spectroscopy and chemical analysis. |
| | Alpha-carrageenan consists of alternating 3-linked β-D-galactopyranosyl and 4-linked 3,6-anhydro--D-galactopyranosyl 2-sulfate residues. | |
| TFP-60 | Ulvan from *Ulva lactuca* | |
| | Origin: | Sample supplied by M Lahaye, INRA, Nantes, France. Prepared by extraction from dried *Ulva lactuca* according to M Lahaye, J. Sci. Food Agric., 54 (1991) 587–594. |
| | Composition: | A soluble xylorhamnoglycurronan sulfate as described in M Lahaye and D Jegon "Chemical and physical-chemical characteristics of dietary fibres from *Ulva lactuca* (L.) Thuret and *Enteromorpha compressa* (L.) Grev.", J. Appl. Phycol., in press. |

The chemical methods used to characterise the above polysaccharides have been detailed in T T Stevenson and R H Furneaux, *Carbohydr. Res.*, 210 (1991) 277–298.

EXAMPLE 10

Chemical Analysis

Samples were analysed for sugar composition, by 13C-NMR spectroscopy and other methods as follows:

Methods (a) Sugar Compositions: Alditol acetate derivatives were prepared from TFP-7 and -9 by the reductive-hydrolysis procedure (T T Stevenson and R H Furneaux, "Chemical Methods for the Analysis of Sulphated Galactans from Red Algae", *Carbohydr. Res.*, 210 (1991) 277–298 and analyzed by capillary g.c. (SP-2330). The observed peak areas were corrected for the known flame ionization detection response factors, and the results are shown in Table 1. Components were identified by retention times alone.

Figure 2:
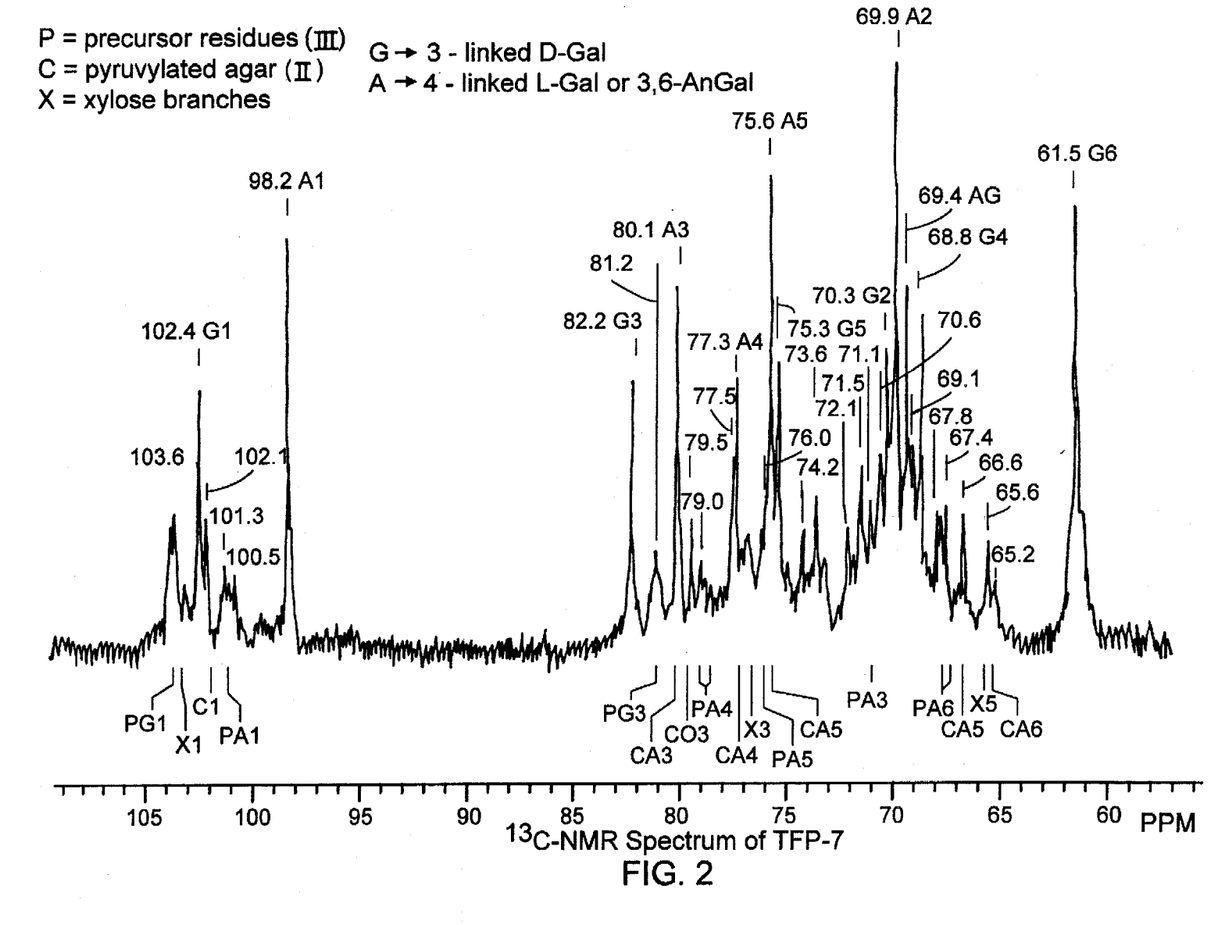
Figure 3:
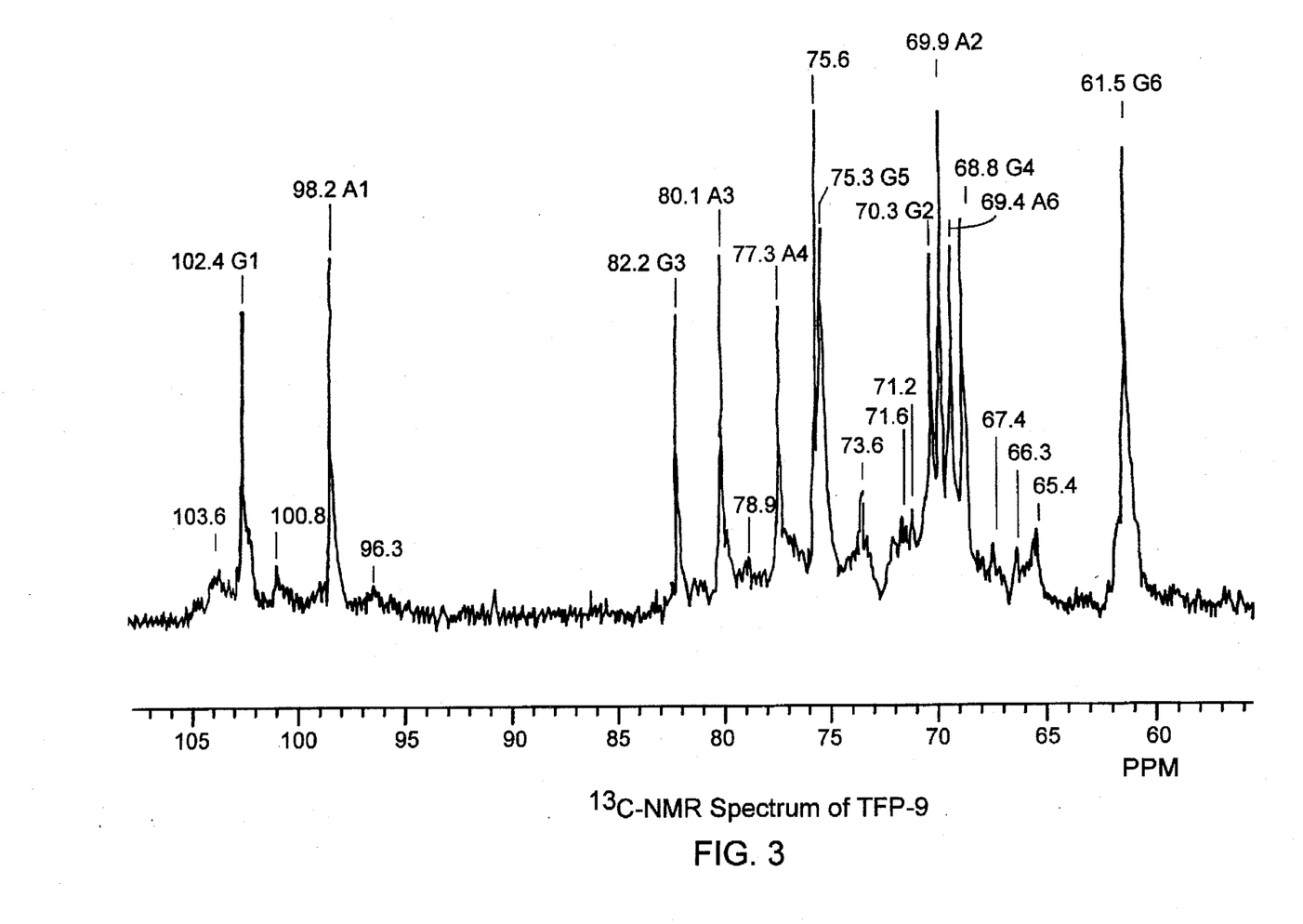

(b) $^{13}$C-NMR Analysis: The spectra of TFP-7 and TFP-9 were recorded on 5–10% solutions in D$_2$O-H$_2$O at 90° C. on a Bruker AC300 spectrometer at 75 MHz and are shown in FIGS. 2 and 3, respectively.

(c) Nitrogen Analyses: Duplicate N-analyses were conducted by the Chemistry Department Microanalytical Facility, University of Otago. The results were:

| | |
|---|---|
| TFP-7 | 0.82, 0.80% |
| TFP-9 | 0.20, 0.25% |

Figure 1:
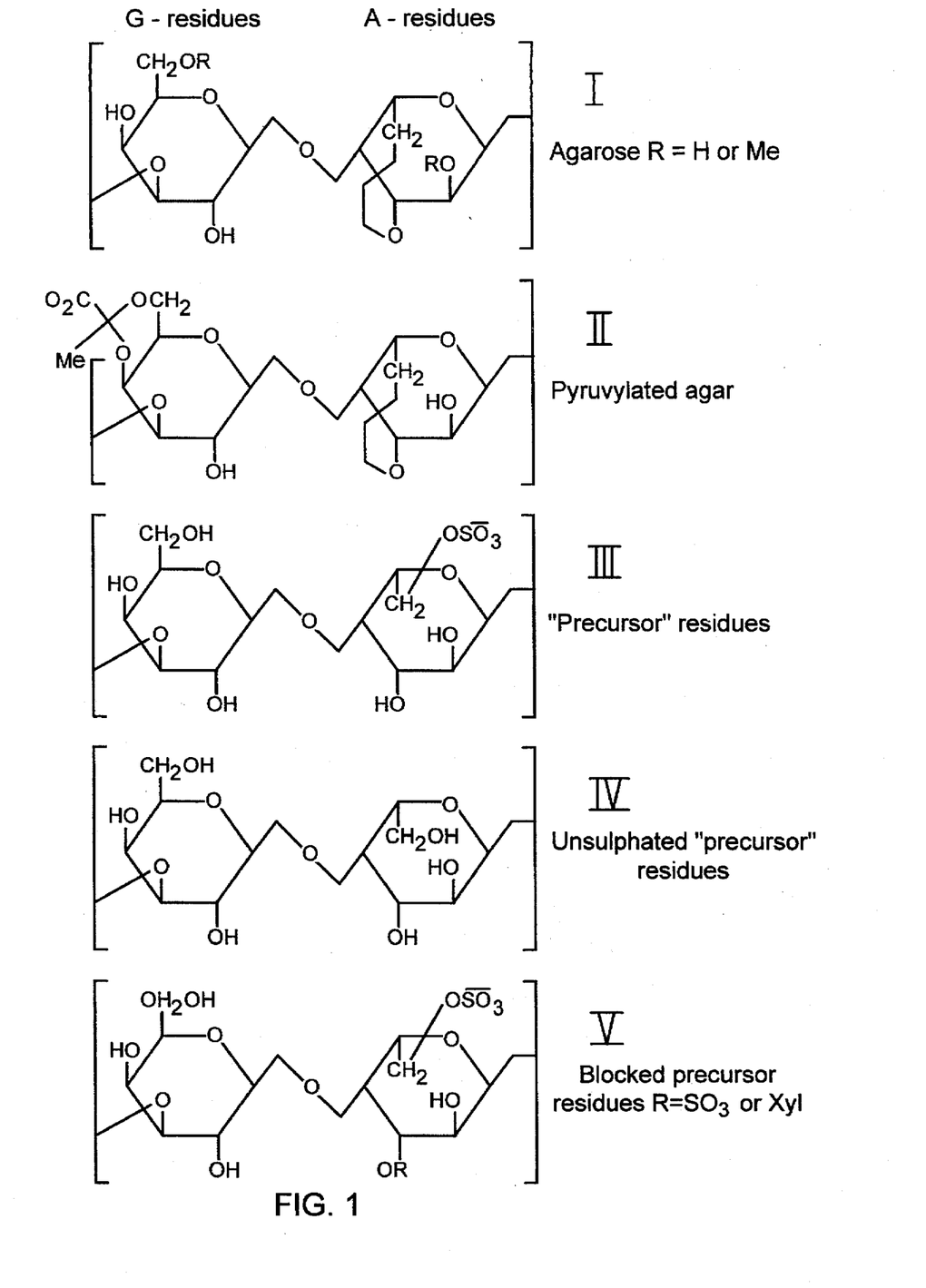

Results from Chemical Analysis i. Structure of TFP-7 and TFP-9: The results are consistent with TFP-7 being an agar-type polymer composed of agarobiose-type repeating units (I and II in FIG. 1) and 'precursor'-type repeating units (III, IV and V in FIG. 1) in the ratio 40:60. TFP-9, formed by alkali treatment of TFP-7, has these repeat units in the ratio 60:40. Thus, of the 60 mol % of 'precursor'-type repeating units originally present, 20 mol % were converted into agarobiose-type units on alkali treatment. Of the agarobiose repeat units in TFP-7 and TFP-9, 4% are methylated at O-2 on the 3,6-anhydrogalactosyl units, 4% are methylated at O-6 on the D-galactosyl units, and a significant but unquantified proportion have a pyruvate ketal unit across O-4 and O-6 of the D-galactosyl unit (Structure II).

The relatively high level of alkali-stable 'precursor'-units is somewhat surprising. These residual units must be of types IV and/or V. In type IV, there is no 6 sulfate group on the 4-linked L-galactosyl unit, so it cannot be eliminated with formation of the 3,6-anhydride. In type V, an alkali-stable residue such as a sulfate group or xylopyranosyl unit, is attached to O-3 of the 4-linked L-galactose residue and thereby blocks 3,6-anhydride formation. Agaroids containing type V residues have been discovered in red algae [R H Furneaux and T T Stevenson, "The xylogalactan sulphate from *Chondria macrocarpa* (Ceramiales, Rhodophyta)", *Hydrobiologia*, 204/205, 1990, 615–620]. Xylosyl residues in agaroids are usually present as single branch residues attached to the main chain; TFP-7 and TFP-9 contain a significant proportion of xylose as a constituent sugar. The precursor residues are methylated to a similar extent and on equivalent positions as for the agarobiose residues, and very likely also contain pyruvate substituents.

The $^{13}$C-NMR spectra are very useful in that, to a considerable extent, they confirm the proposed structures. Layahe and co-workers (*Carbohydr. Res.*, 1989, 190, 249) have published a comprehensive set of chemical shift assignments for substituted agars. In the spectra from both TFP-7 and TFP-9, the 12 major peaks correspond to unsubstituted agarose. The level of methylation is so low that peaks due to these repeat units are not readily identified. Peaks due to repeat units II, III and IV are indicated along with those for single xylosyl branch residues on the spectrum of TFP-7 (FIG. 2). In comparison to the TFP-7 spectrum, the intensity of the minor peaks is reduced relative to those of agar in the TFP-9 spectrum (FIG. 3); e.g. those at 103.6 and 101 ppm, which are broad and largely due to the A1 and G1 signals in the precursor-type repeat units III and IV. In FIG. 3, G1–G6 and A1–A6 indicate agar resonances.

Also observed but not shown in FIGS. 2 and 3 are the characteristic pyruvate ketal resonances which were present at 25.6 and 176 ppm for C-Me and carboxyl, respectively.

ii Proteinaceous components: Nitrogen weight-percent values must be multiplied by a factor to get the protein content. Although this factor varies depending on the aminoacid composition, a representative value of 5.8 is often used. TFP-7 would thus have a protein content of ca 4–5% and TFP-9 about 1%. The alkaline treatment used to produce TFP-9 has thus caused the degradation of 80% of the protein content of TFP-7 such that it is lost on dialysis.

Since alkali-treatment removes most of the protein but does not remove the AVA, it is unlikely that the AVA is a protein or a glycoprotein.

iii Effect of Mild Acid Hydrolysis: TFP-8B was generated by mild acid hydrolysis of TFP-7 (0.1M HCl, 80°, 1 h), neutralization, and dialysis. This treatment removed 68% of the original 3,6-anhydro-galactose content, but did not significantly affect the xylose content, nor in fact any other component. This is the result expected on the basis of the structure proposed for TFP-7 above, if the agarobiose-type residues and the precursor-type residues occur separately in blocks together, or are in separate polymer chains. The observed decrease in 'AnGal' can only occur if agar blocks have been degraded to agarobiose by hydrolysis and these disaccharides are then lost on dialysis.

TABLE 1: Constituent Monosaccharides (relative mol %) determined by g.c. analysis of alditol acetate derivatives.

| Sugar | Retention Time (min) | SAMPLE | | |
|---|---|---|---|---|
| | | TFP-7 | TFP-9 | TFP-8B |
| 2-MeAnGal | 3.7 | 0.8 | 2.0 | 1.1 |
| AnGal | 6.1 | 17.1 | 24.7 | 5.5 |
| 6-MeGal | 6.4 | 1.7 | 1.6 | 1.5 |
| Xyl | 6.7 | 5.3 | 4.5 | 7.2 |
| 2-MeGal | 8.6 | 0.7 | 0.3 | 0.9 |
| Gal | 11.5 | 68.7 | 62.2 | 77.9 |
| Glc | 12.6 | 1.7 | 1.0 | 2.0 |
| Unknown A | 6.9 | 2.0 | 1.9 | 1.5 |
| Unknown B | 10.1 | 0.7 | 0.4 | 0.5 |
| Unknown C | 10.8 | 1.3 | 1.4 | 1.9 |

2-MeAnGal = 3,6-anhydro-2-O-methyl-L-galactose
AnGal = 3,6-anhydro-L-galactose
6-MeGal = 6-O-methyl-D-galactose
Xyl = xylose
2-MeGal = 2-O-methyl-L-galactose
Gal = D- + L-galactose
Glc = D-Glucose

EXAMPLE 11

Demonstration of Anti-Vitrification Effect for *P radiata*

The various AVA samples were incorporated into culture media and tested for their ability to reduce vitrification and hence promote growth of plants.

Media was prepared with modified Quoirin-Le Poirve mineral salt solution, gelled with 0.2% Gelrite (Gellan gum) supplied by Kelco Division of Merck & Co., Kelco, San Diego, Calif., U.S.A. The media contained 5 mg/l benzyl adenine (highly vitrifying mixture). The AVA samples were added to the media prior to autoclaving. The mixtures were sterilized and poured into petri dishes.

Shoot samples for testing were *Pinus radiata* 4 mm stem cuttings. Five clones were assayed, chosen as being more prone to vitrification than average, with 20 shoots in each replica of media being assayed (total 100 shoots per media sample). The base medium, gelled only with Gelrite was used as the control. After setting the shoots, the plates were wrapped and incubated at 25° C. They were subjected to a 16 hour light regime at 40 E/m$^2$/sec. At six weeks, live shoots with no sigh of vitrification were counted to provide the acceptable shoot number. Shoots suffering from either toxicity or vitrification are excluded from the acceptable shoot tally, therefore toxicity as well as AVA influences are tested. Selected results are shown in Table 3.

TABLE 3

RELATIVE ACTIVITY OF AVA SAMPLES

| SAMPLE | Code Name | ml or g/ 200 ml | Assay No. | Best Result[a] | Control[b] |
|---|---|---|---|---|---|
| DIALYSED AQ. EXTRACT DIFCO | TFP-7 | 0.55 | 1 | 88 | 14 |
| DIALYSED DIFCO EXTR. ALKALI TREATED | TFP-9 | 0.42 | 1 | 80 | 14 |
| EUCHEUMA CARRAG. | CBL10 | 0.54 | 7 | 97 | 10 |
| GIGARTINA DECIPIENS LAMBDA CARRAG. | TFP-33J | 0.27 | 4 | 70 | 5 |
| AEODES SP. | TFP-38A | 0.54 | 5 | 92 | 1 |
| DIFCO EXTRACT (9) 83% ETOH | TFP-25A | 0.14 | 3 | 79 | 0 |
| CHONDRUS CRISPUS LAMBDA CARRAG. | TFP-39F | 1.08 | 6 | 74 | 4 |
| DIFCO EXTRACT (9) 95% ETOH | TFP-25B | 0.06 | 3 | 78 | 0 |
| DEXTRAN SO4-D6001 MW 500,000 | TFP-39E | 0.54 | 5 | 86 | 1 |
| DEXTRAN SO4.D7140 MW 500,000 | TFP-39B | 0.54 | 5 | 75 | 1 |
| DEXTRAN SO4-D4911 MW 800 | TFP-39D | 0.54 | 5 | 52 | 1 |
| DEXTRAN SO4-D7037 WM 50000 | TFP-39C | 0.27 | 5 | 44 | 1 |
| VISCARIN LOT 952701 | GP 309 | 1.08 | 9 | 95 | 0 |
| SODIUM CELLULOSE SULPHATE LOT 89010B | TFP-46A | 0.22 | 10 | 69 | 29 |
| GIGARTINA CIRCUMCINCTA TETRASPORITE | TFP-50 | 0.54 | 9 | 73 | 0 |
| GIGARTINA CIRCUMCINCTA CYSTOCARPIC | TFP-48 | 0.54 | 9 | 69 | 0 |
| EUCEUMA COTTONII IOTA CARRAGEENAN | TFP-49A | 0.54 | 9 | 93 | 0 |
| GIGARTINA DECIPIENS | TFP-47 | 0.54 | 9 | 67 | 0 |
| ORAKEI WEED IOTA CARRAGEENAN | TFP-57A | 0.81 | 12 | 90 | 10 |
| ORAKEI WEED ALKALI MODIFIED | TFP-57B | 0.81 | 12 | 95 | 10 |
| SPLACHNIDIUM NEGOSUM FUCOIDIN | TFP-56 | 0.81 | 12 | 84 | 10 |
| GIGARTINA RADULA | TFP-55 | 0.81 | 12 | 93 | 10 |
| CHONDRUS ARMATUS KAPPACARRAGEENAN Grade A | TFP-51A | 0.81 | 12 | 93 | 10 |
| CHONDRUS ARMATUS KAPPACARRAGEENAN Grade B | TFP-51B | 0.54 | 12 | 90 | 10 |
| CATANELLA | TFP-39 | 1.08 | 13 | 85 | 3 |
| ULVA LACTUCA ULVAN | TFP-60 | 0.54 | 13 | 86 | 3 |
| AQUEOUS EXTRACT OF DIFCO BACTO AGAR ACID TREATED | TFP-8A | 0.59 | 1 | 46 | 3 |
| AQUEOUS EXTRACT OF DIFCO BACTO AGAR ACID TREATED AND DIALYSED | TFP-8B | 0.38 | 1 | 44 | 3 |
| SARCODIA FLABELLATA GALACTAN | TFP-26B | 0.2 | 3 | 84 | 0 |
| SIGMA LAMBDA CARRAGEENAN | TFP-26C | 0.56 | 3 | 53 | 0 |
| CHONDRIA MACROCARPA | TFP-26F | 0.31 | 3 | 74 | 0 |
| GELIDIUM AGAR (LOT 2242) MATRIX | TFP-32A | 0.4 | 4 | 26 | 0 |
| GELIDIUM AGAR (LOT 2242) AQUEOUS LEACHATE | TFP-32B | 0.4 | 4 | 43 | 0 |
| SIGMA IOTA CARRAGEENAN | TFP-33C | 0.54 | 4 | 60 | 0 |
| SIGMA KAPPA CARRAGEENAN | TFP-33D | 0.54 | 4 | 38 | 0 |
| PORPHYRAN | TFP-33E | 0.54 | 4 | 51 | 0 |
| GRATALOUPIA PINATA | TFP-33F | 0.27 | 4 | 51 | 0 |
| GRATALOUPIA INTASTINALIS | TFP-33G | 0.27 | 4 | 70 | 0 |
| GELIDIUM PRESSED FLUID | TFP-35 | 0.4 | 5 | 79 | 1 |
| GIGARTINA CHAPMANII LAMBDA CARRAGEENAN | TFP-37A | 0.54 | 5 | 69 | 1 |
| GIGARTINA CLAVERFERI LAMBDA CARRAGEENAN | TFP-37B | 0.54 | 5 | 86 | 1 |
| PACHYMENIA POLYSACCHARIDE | TFP-38B | 0.54 | 5 | 84 | 1 |
| PENTOSAN POLYSULFATE | TFP-39A | 0.54 | 5 | 34 | 1 |
| EUCEUMA COTTONII KAPPA CARRAGEENAN | TFP-49B | 0.54 | 9 | 32 | 0 |
| PTERACLADIA PRESSED FLUID - DIALYSED | TFP-14B | 0.22 | 2 | 79 | 21 |
| PTERACLADIA PRESSED FLUID - CRUDE | TFP-14A | 0.26 | 2 | 54 | 21 |

[a]Best Result = Percent of shoots showing no vitrification at the rate of application of AVA indicated, this being the lowest rate for optimum activity
[b]Control = Percent of shoots showing no vitrification in a given bioassay when using Gelrite alone.

EXAMPLE 12

Demonstration of Anti-vitrification Effect for Eucalyptus Species

Prepare Basal salt medium with benzyl adenine and napthalene acetic acid, plus 2% sucrose.

Divide into four equal portions and add gelling agents and AVA as follows:

a) Basal medium plus 0.7% BBl Agar
b) Basal medium plus 0.25% Gelrite
c) Basal medium plus 0.25% Gelrite plus 0.27% Dextran Sulphate
d) Basal medium plus 0.25% Gelrite plus 0.27% Viscarin GP309*

* Predominantly lambda carrageenan, with some kappa carrageenan.

Vitrification was evaluated after six weeks incubation on these media.

| Results | | % Vitrified Shoots |
|---|---|---|
| a) | BBL agar | 40 |
| b) | Gelrite | 80 |
| c) | Gelrite plus Dextran Sulphate | 47 |
| c) | Gelrite plus Viscarin GP309 | 15 |

EXAMPLE 13

To demonstrate the advantage of removing toxic substances, a first sample from Pterocladia, press fluid, freeze dried, TFP 14A was tested under the same conditions of Example 16, at a concentration of 0.26 g/ml. Assay 2 gave a best result of 54 whereas the control was only 3. When this material was dialysed and freeze-dried to give sample TFP-14B and tested at a concentration of 0.22 g/200 ml, assay 2 gave a best result of 79 while the control was 3.

This example shows that by removing low molecular weight substances such as by dialysis, the anti-vitrification of the substances obtained from seaweed can be enhanced, through detoxification.

It is to be understood that the scope of the invention is not limited to the described embodiments and therefore that numerous variations and modifications may be made to these embodiments without departing from the scope of the invention as set out in the specification.

We claim:

1. A method for inhibiting vitrification comprising growing a species of Pinus or a species of Eucalyptus using a tissue culture media to which an anti-vitrification agent has been added, said anti-vitrification agent comprising a purified sulfated polysaccharide, substantially free of toxic components, or a mixture of purified sulfated polysaccharides substantially free of toxic components.

2. A method according to claim 1 wherein the sulfated polysaccharide has a degree of sulfation greater than 10%.

3. The method according to claim 2 wherein the sulfated polysaccharide is extracted from seaweed.

4. The method according to claim 2 wherein the sulfated polysaccharide is obtained from a seaweed of the species Gelidium, Eucheuma, (or Kappaphycus), Chondrus, Aodies, Pterocladia, Sarcodia, Melanthalia, Gracilaria, Curdiea, Porphyra, Grateloupia, Gigartina, Chondria, Pachymenia, Iridea, Splachnidium, Catenella, Ulva, or Sarcodiotheca.

5. The method according to claim 2 wherein the sulfated polysaccharide is selected from the group consisting of carrageenans, sulfated dextrans and sulfated celluloses.

6. The method according to claim 5 wherein the sulfated polysaccharide is a carrageenan.

7. The method according to claim 5 wherein the carrageenan is a kappa lambda, iota or precursor rich mu or precursor rich nu carrageenan.

8. The method according to claim 2 wherein the sulfated polysaccharide is dextran sulfate.

9. The method according to claim 2 wherein each saccharide unit has one or more sulfate half ester group.

10. The method according to claim 2 wherein the polysaccharide is selected from the group consisting of fucans, galactans, xyloramnoglycuronans and glucans.

11. The method according to claim 2 wherein the polysaccharide has substituents selected from methyl groups and sugars.

12. The method according to claim 10 wherein the polysaccharide is xylose.

13. The method as claimed in claim 2 wherein the species of Pinus is P. radiata.

14. A tissue culture medium comprising growth medium for a species of Pinus and a purified sulfated polysaccharide or a mixture of purified sulfated polysaccharides, wherein the sulfated polysaccharide or mixtures thereof are substantially free of toxic components and wherein the sulfated polysaccharide has a degree of sulfation greater than 10%.

15. A tissue culture medium comprising growth medium for a species of Eucalyptus and a purified sulfated polysaccharide or a mixture of purified sulfated polysaccharides, wherein the sulfated polysaccharide or mixtures thereof are substantially free of toxic components and wherein the sulfated polysaccharide has a degree of sulfation greater than 10%.

16. A tissue culture medium according to claim 14 wherein the sulfated polysaccharide is selected from the group consisting of carrageenans, sulfated dextrans and sulfated celluloses.

17. A tissue culture medium according to claim 15 wherein the sulfated polysaccharide is selected from the group consisting of carrageenans, sulfated dextrans and sulfated celluloses.

18. In the propagation of trees of the Pinus species or Eucalyptus species by tissue culture methods, the improvement comprising adding a purified sulfated polysaccharide or a mixture of purified sulfated polysaccharides to a tissue culture medium wherein the sulfated polysaccharide or the mixtures of sulfated polysaccharides are substantially free of toxic components and wherein the sulfated polysaccharide has a degree of sulfation greater than 10%.

19. A method according to claim 2 wherein the tissue culture medium is a gel and the sulfated polysaccharide or mixtures thereof are incorporated into the gel on which the species of Pinus or species of Eucalyptus is to be grown.

20. A method according to claim 2 wherein the tissue culture medium is a liquid and the sulfated polysaccharide or mixtures thereof are incorporated into the liquid media in which the species of Pinus or species of Eucalyptus is to be grown.

21. A method for inhibiting vitrification which comprises growing a species of Pinus or a species of Eucalyptus using a tissue culture media to which an anti-vitrification agent dextran sulfate has been added.

22. A tissue culture medium comprising growth medium for a species of Pinus and dextran sulfate.

23. A tissue culture medium comprising growth medium for a species of Eucalyptus and dextran sulfate.

24. The method according to claim 2 wherein the sulfated polysaccharide is obtained from a seaweed of a member of Solieriaceae.

* * * * *